United States Patent
Fang et al.

(10) Patent No.: US 10,188,768 B2
(45) Date of Patent: Jan. 29, 2019

(54) MINIATURE SCENT GENERATING DEVICE

(75) Inventors: Wei-Ieun Fang, Hsinchu (TW); Heng-Chung Chang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 811 days.

(21) Appl. No.: 13/607,742

(22) Filed: Sep. 9, 2012

(65) Prior Publication Data

US 2013/0292486 A1    Nov. 7, 2013

(30) Foreign Application Priority Data

May 3, 2012   (TW) .............................. 101115728 A

(51) Int. Cl.
    *A61L 9/12*    (2006.01)
(52) U.S. Cl.
    CPC ........... *A61L 9/125* (2013.01); *A61L 2209/11* (2013.01); *A61L 2209/132* (2013.01)
(58) Field of Classification Search
    CPC . A61L 9/125; A61L 2209/132; A61L 2209/11
    USPC ............. 239/4, 34, 35, 58–59, 102.1, 102.2, 239/44–45, 436, 441, 448–449
    See application file for complete search history.

(56) References Cited

U.S. PATENT DOCUMENTS

| | | |
|---|---|---|
| 2004/0203412 A1 | 10/2004 | Greco et al. |
| 2006/0293871 A1* | 12/2006 | Fazzio ................... A61L 9/035 703/5 |
| 2007/0075159 A1* | 4/2007 | Lin ........................... A61L 9/12 239/60 |
| 2009/0108094 A1* | 4/2009 | Ivri .......................... A61L 9/14 239/101 |
| 2009/0253612 A1* | 10/2009 | Mushock .................. A23L 2/39 512/4 |
| 2011/0217211 A1 | 9/2011 | Park et al. |
| 2011/0266359 A1* | 11/2011 | Haran .............................. 239/6 |

FOREIGN PATENT DOCUMENTS

JP    2004121594    *  4/2004    ............... A61L 9/12

* cited by examiner

*Primary Examiner* — Darren W Gorman
*Assistant Examiner* — Qingzhang Zhou
(74) *Attorney, Agent, or Firm* — Chun-Ming Shih; HDLS IPR Services

(57) ABSTRACT

A miniature scent generating device includes a scented component, a plurality of granular first materials, and a driving unit. The scented component includes a housing, a chamber located in the housing, a ventilation opening penetrating through the housing to communicate with the chamber, and a vibration unit disposed in the chamber. The first materials are provided in the chamber, and have a first scent. The driving unit is connected to the vibration unit. The vibration unit is controlled by the driving unit to vibrate and produce an airflow of perturbation in the chamber, so as to prompt the first materials to pass through the ventilation opening and discharge out of the chamber to disperse the first scent. The miniature scent generating device has the advantage of unlikely spoiled and readily controlling a release concentration of the scent.

14 Claims, 7 Drawing Sheets

MINIATURE SCENT GENERATING DEVICE

FIELD OF THE INVENTION

The present invention relates to a scent generating device, and particularly to a miniature scent generating device applied in a mobile device.

BACKGROUND OF THE INVENTION

A conventional scent releasing device usually offers non-ideal portability as being large in volume, and provides a scent limited to a perfume or essence carried in the scent releasing device. Accompanied with the flourish of electronic products, various portable electronic devices are now an indispensable part of the daily life. In nowadays, portable electronic devices indeed fulfill consumer needs with respect to visual, audio and tactile aspects. However, portable electronic devices developed towards a direction of smell are quite meager.

As technologies develop continually, miniature scent releasing devices applicable to a portable electronic device are proposed progressively. For example, an U.S. Pat. Pub. No. US2004/0203412 discloses a communication device capable of releasing a scent. A scented substance is located on a heat-generating device, which produces heat energy that activates the scented substance and causes a scent to be released from the scented substance as the heat-generating device is operated.

In an U.S. Pat. Pub. No. US2011/0217211, a smell-diffusing structure comprising a photocatalyst applicable to a portable electronic device is disclosed. A scented substance is carried in a microcapsule formed by the photocatalyst. When being exposed by ultraviolet light or another light source having a predetermined wavelength, the scented substance in the microcapsule is diffused to the external to spread a scent.

In the above conventional techniques for releasing a scent of a perfume or substance by mean of heating, the perfume or substance has a tendency of spoilage due to frequent heating. Further, in the approach of releasing a scent through the photocatalyst microcapsule, not only an additional light source is needed but also a release amount of the scented substance cannot be easily controlled. Therefore, there is a solution for alleviating or eliminating the above issues.

SUMMARY OF THE INVENTION

Therefore the primary object of the present invention is to overcome issues of a tendency of spoilage due to frequent heating, an additional lighting source required for triggering the photocatalyst and a complication in controlling the release amount of a scented substance as in the prior art.

To achieve the above object, a miniature scent generating device is provided by the disclosure. The miniature scent generating device comprises a scented component, a plurality of granular first materials, and a driving unit. The scented component comprises a housing, a chamber located in the housing, a ventilation opening penetrating through the housing to communicate with the chamber, and a vibration unit disposed in the chamber. The first materials are located in the chamber and have a first scent. The driving unit is connected with the vibration unit.

The vibration unit is controlled by the driving unit to induce an airflow of perturbation in the chamber, so as to prompt the first materials to pass through the ventilation opening to disperse the first scent.

The disclosure further provides a miniature scent generating device. The miniature scent generating device comprises a plurality of scented components, a plurality of granular first materials, a plurality of granular second materials, and a driving unit. The scented components, provided in an array arrangement, respectively comprise a housing, a chamber located in the housing, a ventilation opening penetrating the housing to communicate with the chamber, and a vibration unit disposed in the chamber. The first materials and the second materials are respectively disposed in the chambers of the corresponding scent, and respectively have a first scent and a second scent. The driving unit is connected with the vibration unit.

The vibration unit is controlled by the driving unit to produce a vibration to induce an airflow of perturbation in the chamber, so as to prompt the first materials and the second materials to pass through the ventilation opening to be discharged out of the chamber and be blended into a mixed scent.

Accordingly, with the design of the granular first materials and the vibration unit of the disclosure, the first scent is released through the airflow of perturbation. Therefore, the disclosure is free from issues of having a tendency of spoilage due to frequent heating, needing an additional lighting source required for triggering the photocatalyst and suffering a complication in controlling the release amount of a scented substance. Further, by providing the first materials and the second materials possessing different scents in the scented components in an array arrangement, the blended scent may also be achieved.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 1A:
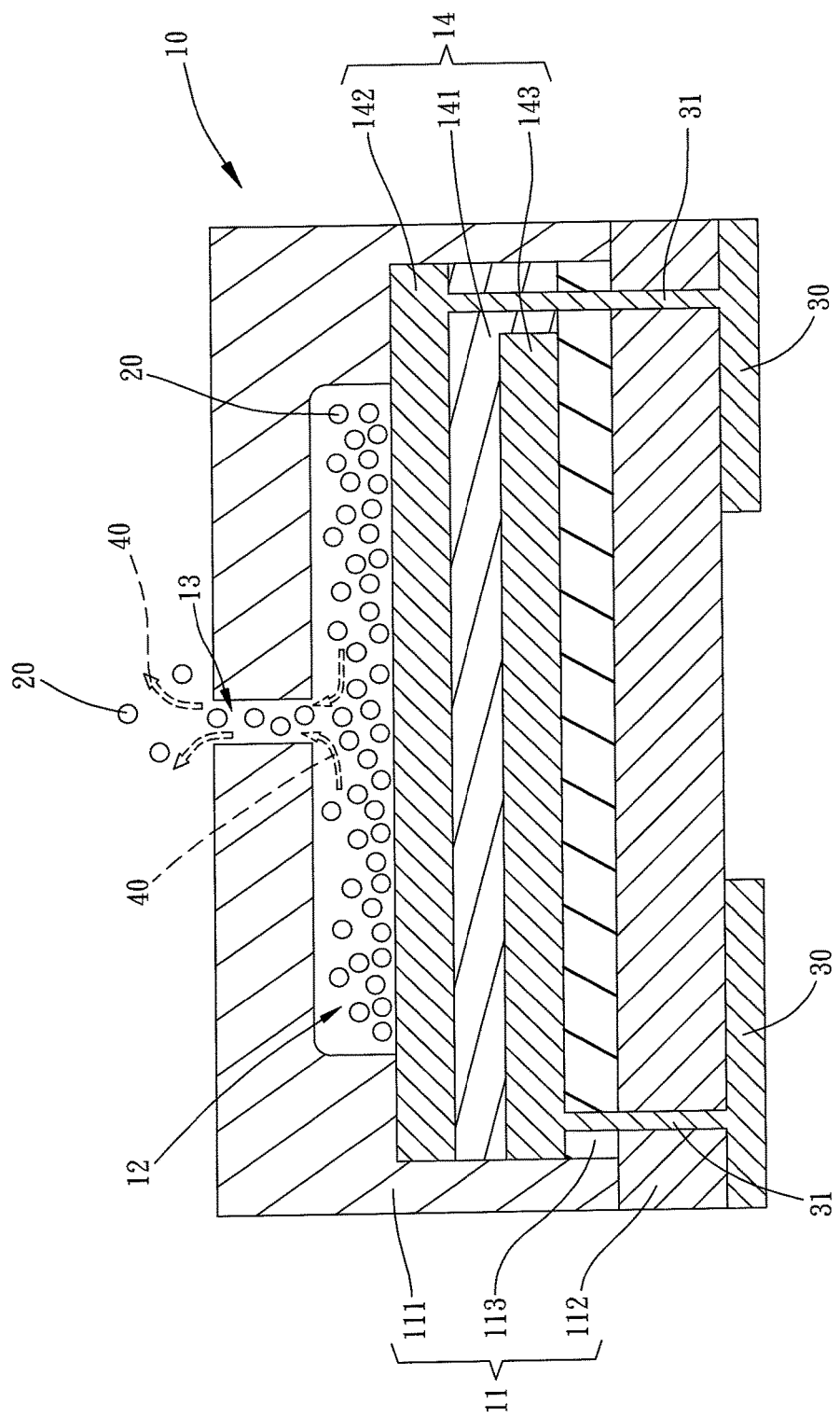
FIG. 1A is a schematic diagram of a structure according to a first embodiment of the disclosure.
Figure 1B:
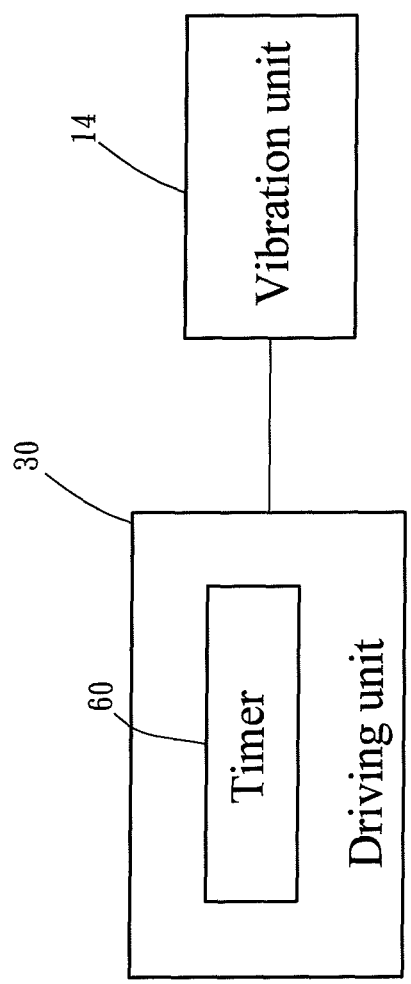
FIG. 1B is a schematic diagram of electrical connections of a driving unit according to the first embodiment of the disclosure.

FIG. 1A shows a schematic diagram of a structure according to a first embodiment of the disclosure. FIG. 1B shows a schematic diagram of electrical connections of a driving unit according to the first embodiment of the disclosure. According to an embodiment of the disclosure, a miniature scent generating device comprises a scented component 10, a plurality of granular first materials 20 and a driving unit 30. The scented component 10 comprises a housing 11, a chamber 12, a ventilation opening 13 and a vibration unit 14. The chamber 12 is located in the housing 11. The ventilation opening 13 penetrates through the housing 11 to communicate with the chamber 12. The vibration unit 14 is disposed in the chamber 12. In this embodiment, the housing 11 comprises an upper housing 111, and a lower housing 112 corresponding to the upper housing 111. For example, the lower housing 111 could be a silicon chip. The ventilation opening 13 penetrates through the upper housing 111, and the chamber 12 is located between the upper housing 111 and the lower housing 112. The housing 11 further comprises an insulation layer 113, which is disposed between the lower housing 112 and the vibration unit 14 to insulate the vibration unit 14 from the lower housing 112. It should be noted that, the structure of the foregoing scented component may be fabricated by a micro electrical mechanical system (MEMS) process to achieve a miniaturized design.

The first materials 20 located in the chamber 12 have a first scent. For example, the first materials 20 could be solid-state scented particles or microcapsules encapsulating essences. The driving unit 30 is connected with the vibration unit 14. The driving unit 30 comprises a control circuit, and is disposed outside the housing 11 to be connected to the lower housing 112. Based on an MEMS process, a hole could be formed at the lower housing 112, and an internal wire 31 is made to embed into the lower housing 112 to become electrically connected to the vibration unit 14. It should be noted that, the electrical connections are not limited to the approach of the internal wire 31, but may also be accomplished via a common metal wire.

In the first embodiment, the vibration unit 14 comprises a piezoelectric film 141, a first electrode 142 and a second electrode 143. For example, the piezoelectric film 141 is made of a piezoelectric material selected from aluminum nitride, zinc oxide, lithium niobate, lithium tantalate, lead zirconate titanate, and quartz. The first electrode 142 and the second electrode 143 are connected to the piezoelectric film 141 as well as electrically connected to the driving unit 30. For example, the first electrode 142 and the second electrode 143 are made of a metal selected from aluminum, copper, tungsten, silver and gold. The first electrode 142 and the second electrode 143 are respectively disposed at an upper side and a lower side of the piezoelectric film 141 in a layered configuration, in a way that the piezoelectric film 141 is located between the first electrode 142 and the second electrode 143. Further, the first electrode 142 and the second electrode 143 may also respectively appear as a plurality of interdigital shapes disposed in a staggered arrangement at a same side of the piezoelectric film 141.

In the first embodiment, when the miniature scent generating device is activated, an alternating current (AC) power is provided by the driving unit 30 from the first electrode 142 to the second electrode 143 to cause a varying electric field between the first electrode 142 and the second electrode 143. Being made of a piezoelectric material, the piezoelectric 141 periodically expands and contracts due to the varying electric field to further produce a vibration. Thus, the vibration induces an airflow 40 of perturbation in the chamber 12, and the airflow 40 carries the first materials 20 to pass through the ventilation opening 13. When the first materials 20 are the solid-state scented particles, the first materials 20 are discharged out of the housing 11 to disperse the first scent in the surrounding air. When the first materials 20 are the microcapsules encapsulating the essences, the first scent is released from the essences to the air as the microcapsules are broken due to impact, abrasion or vibration in the process of discharging out of the housing 11. Further, it should be noted that, the driving unit 30 further comprises a timer 60, according to which the driving unit 30 controls a vibration period of the vibration unit 14. Therefore, a release amount of the first materials 20 is controlled by time in order to adjust a release concentration of the first scent in the air.

Figure 2:
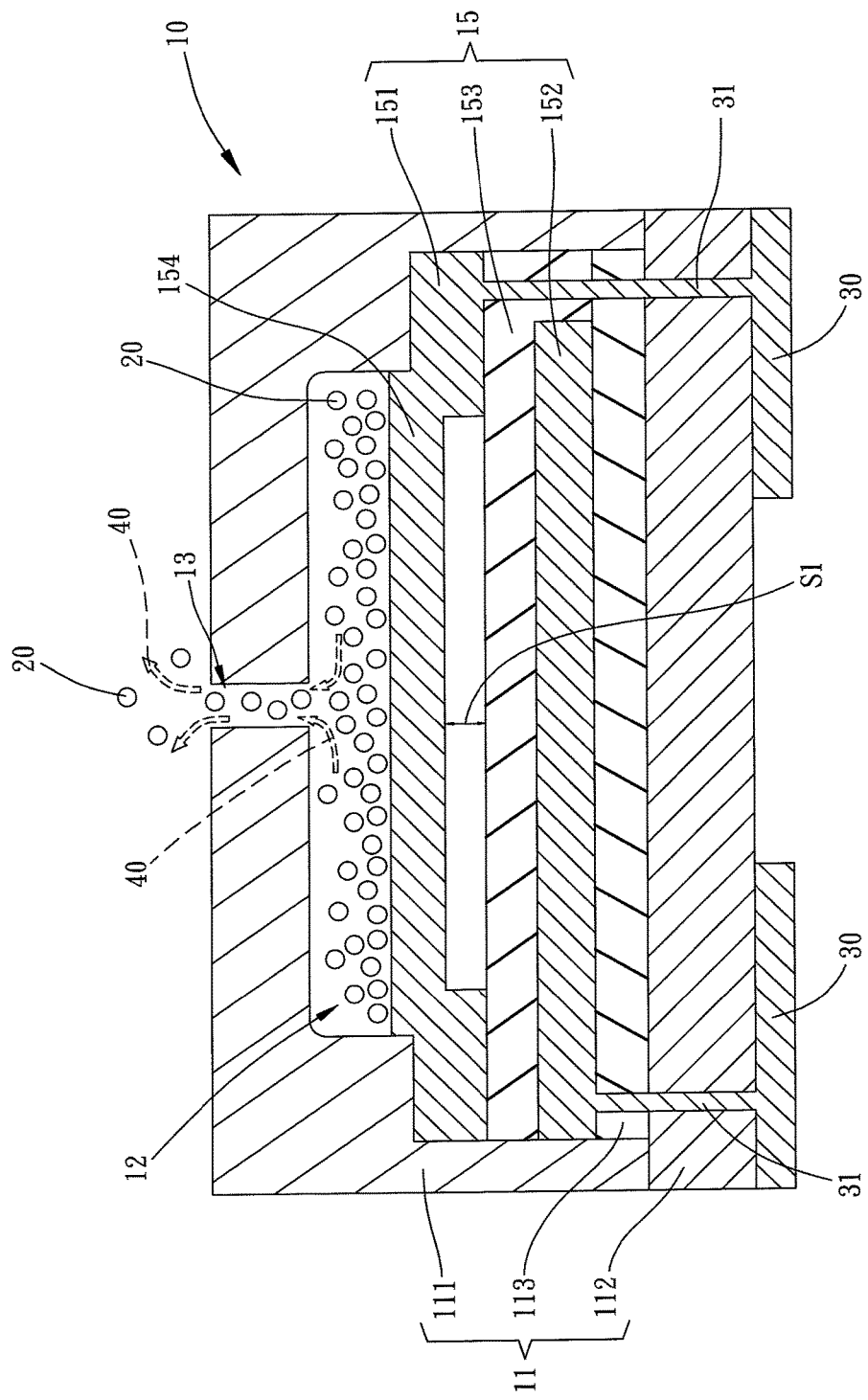
FIG. 2 is a schematic diagram of a structure according to a second embodiment of the disclosure.

FIG. 2 shows a schematic diagram according to a second embodiment of the disclosure. Compared to the first embodiment, in the second embodiment, the vibration unit 14 comprises a first conductive layer 151, a second conductive layer 152 and an insulation film 153. The insulation film 153 is disposed between the first conductive layer 151 and the second conductive layer 152. The first conductive layer 151 is located above the insulation film 153, and comprises a vibration section 154 that is spaced from the insulation film 153 by a vibration interval S1. The second conductive layer 152 is located between the insulation film 153 and the insulation layer 113. Further, the first conductive layer 151 and the second conductive layer 152 are electrically connected to the driving unit 30.

In the second embodiment, when the miniature scented generating device is activated, the driving unit 30 provides a varying voltage to the first conductive layer 151 and the second conductive layer 152 to cause a static electric field between the first conductive layer 151 and the second conductive layer 152. Thus, under the influence of the static electric field between the first conductive layer 151 and the second conductive layer 152, an attraction force is produced periodically between the conductive layer 151 and the second conductive layer 152, such that the conductive layer 151 and the second conductive layer 152 relatively move back and forth and impel the vibration section 153 to produce the vibration. Therefore, the airflow 40 of perturbation is generated to discharge the first materials 20 out of the housing 11 to disperse the first scent in the surrounding air.

Figure 3:
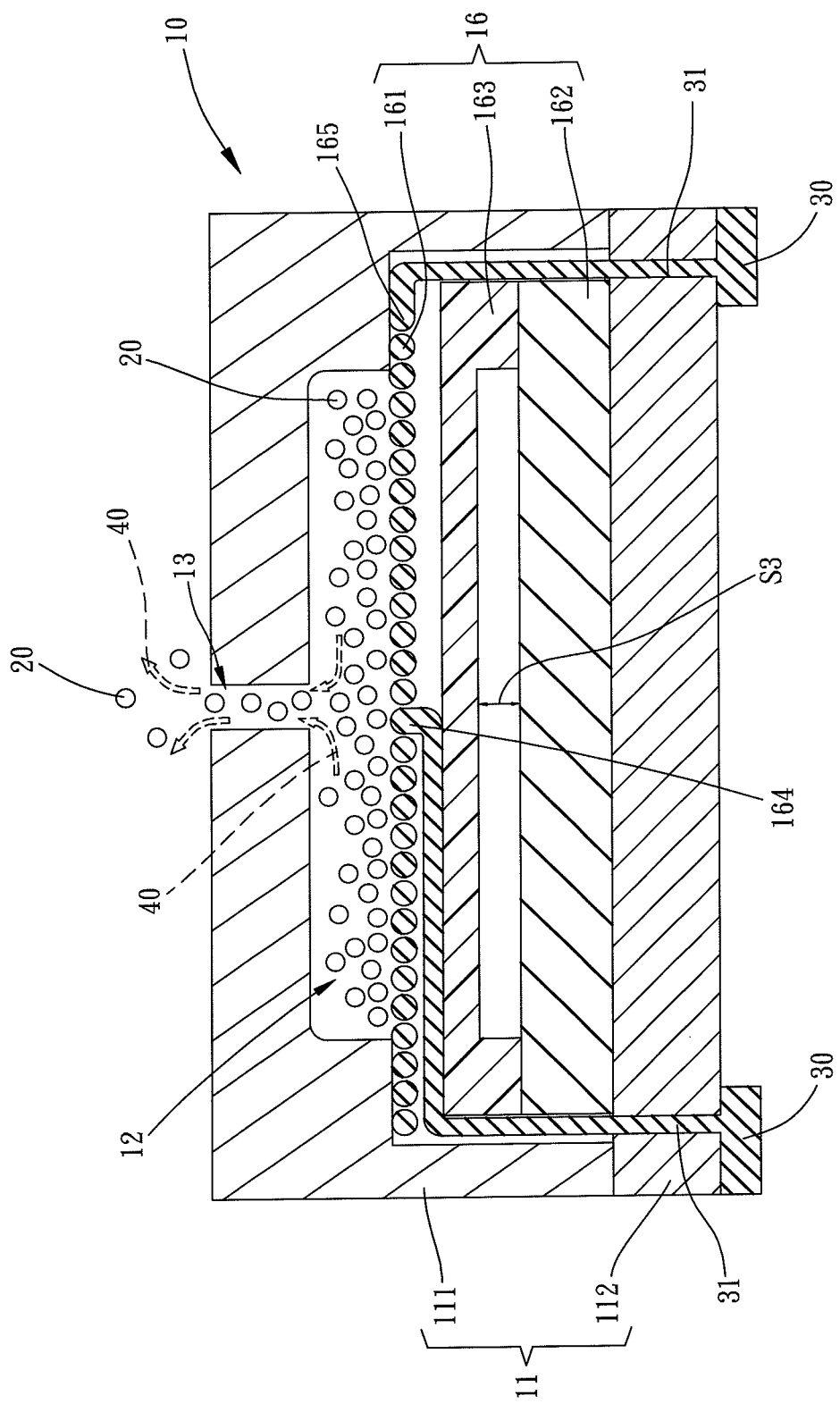
FIG. 3 is a schematic diagram of a structure according to a third embodiment of the disclosure.

FIG. 3 shows a schematic diagram of a structure according to a third embodiment of the disclosure. Compared to the first embodiment, in the third embodiment, a vibration unit 16 comprises a spiral coil 161, a ferromagnetic layer 162, and a vibration film layer 163 disposed between the spiral coil 161 and the ferromagnetic layer 162. The vibration film layer 163 is spaced from the ferromagnetic layer 162 by a vibration interval S3. The spiral coil 161, located on the vibration film layer 163, has a center as a starting terminal 164 and coils from inwards to outwards in a horizontal plane to form an end terminal 165 at an outermost point. The end terminal 165 is electrically connected to the driving unit 30, and the starting terminal 164 is extended to be also electrically connected to the driving unit 30. For example, the ferromagnetic layer 162 could be a magnetic material such as a metal or a multicomponent alloy selected from iron, nickel or cobalt. The vibration film layer 163 may be an insulation material for disconnecting electricity between the spiral coil 161 and the ferromagnetic layer 162.

In the third embodiment, when the miniature scent generating device is activated, the driving unit 30 provides a varying current to the spiral coil 161. The varying current causes the spiral coil 161 to generate a varying magnetic field along an axial direction, such that an attraction force and a repulsion force are periodically generated between the spiral coil 161 and the ferromagnetic layer 162 below the spiral coil 161. Under the influence of the attraction force and repulsion force, the vibration film layer 163 periodically vibrates back and forth. Therefore, the airflow 40 of perturbation is generated to discharge the first materials 20 out of the housing 11 to disperse the first scent in the surrounding air.

Figure 4:
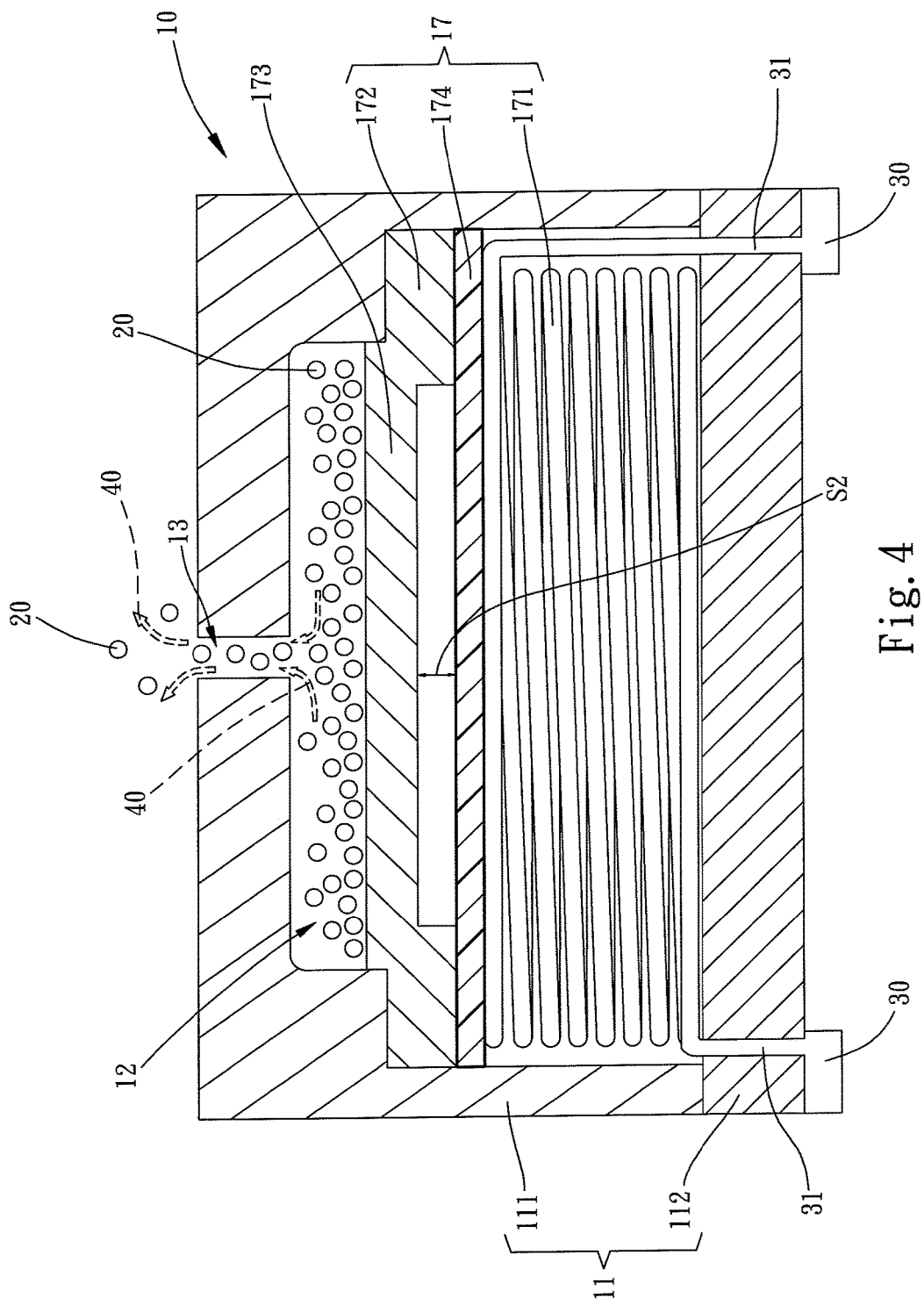
FIG. 4 is a schematic diagram of a structure according to a fourth embodiment of the disclosure.

FIG. 4 shows a schematic diagram of a structure according to a fourth embodiment of the disclosure. Compared to the first embodiment, in the fourth embodiment, a vibration unit 17 comprises an electromagnetic coil 171, a magnetism-receiving film 172, and an insulation film layer 173 between the electromagnetic coil 171 and the magnetism-receiving film 172. The magnetic coil 171 is electrically connected to the driving unit 30. The magnetism-receiving film 172 is disposed above the electromagnetic coil 171, and comprises a vibration section 173 spaced from the insulation film layer 174 by a vibration interval S2. For example, the magnetism-receiving film 172 could be a magnetic material such as a metal or a multicomponent alloy selected from iron, nickel or cobalt.

In the fourth embodiment, when the miniature scent generating device is activated, the driving unit 30 provides a varying current to the electromagnetic coil 171. The varying current causes the electromagnetic coil 171 to generate a varying magnetic field along an axial direction or the electromagnetic coil 171. Under the influence of the attraction and repulsion of the varying magnetic field, the magnetism-receiving film 172 periodically moves back and forth to propel the vibration section 173 to produce the vibration. Therefore, the airflow 40 of perturbation is generated to discharge the first materials 20 out of the housing 11 to disperse the first scent in the surrounding air. It should be noted that, in this embodiment, a core encircled by the electromagnetic coil 171 may also be provided, so that the varying magnetic field is enhanced via the core magnetized by the electromagnetic coil 171.

Figure 5A:
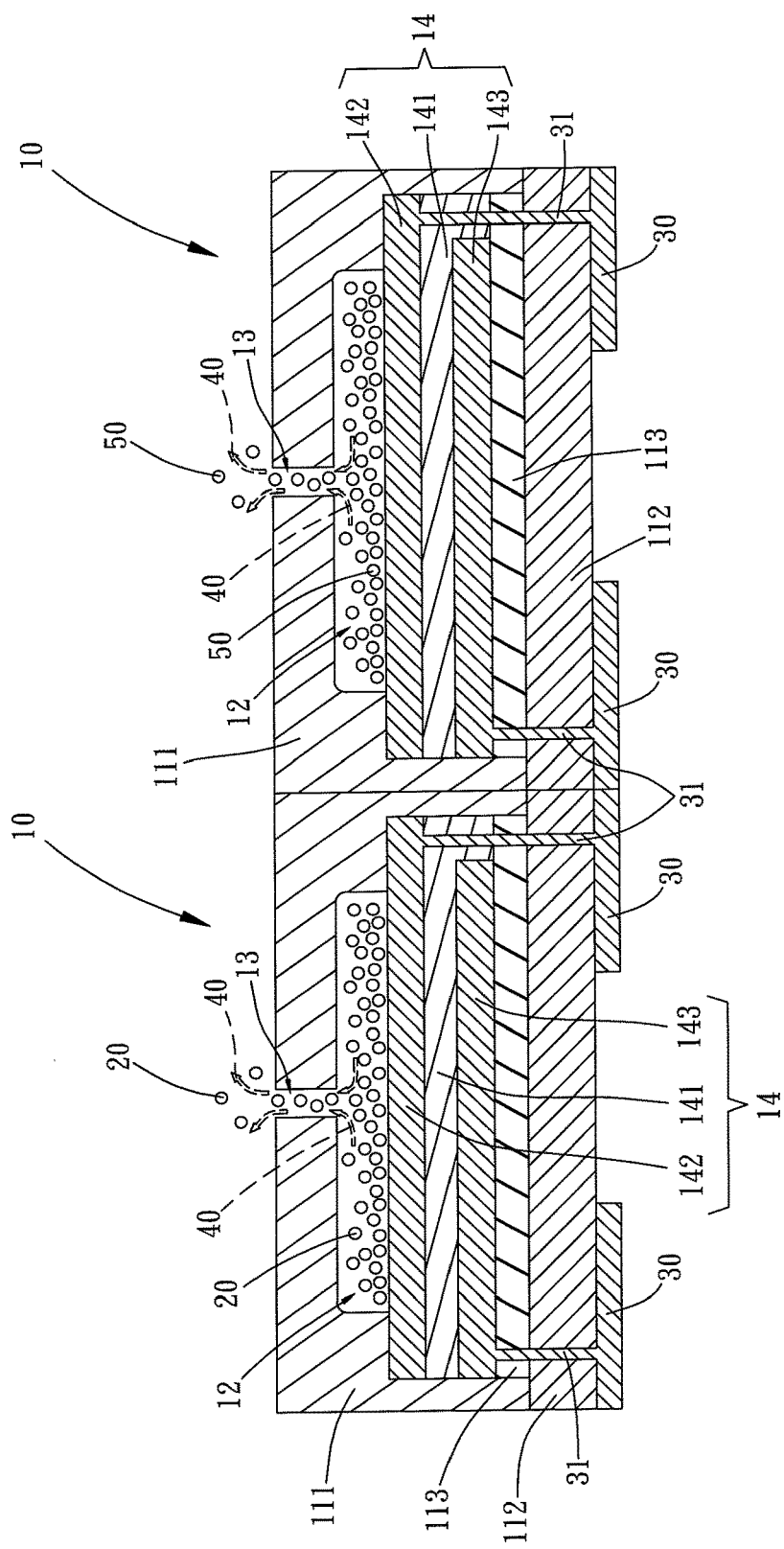
FIG. 5A is a schematic diagram of a structure according to a fifth embodiment of the disclosure.
Figure 5B:
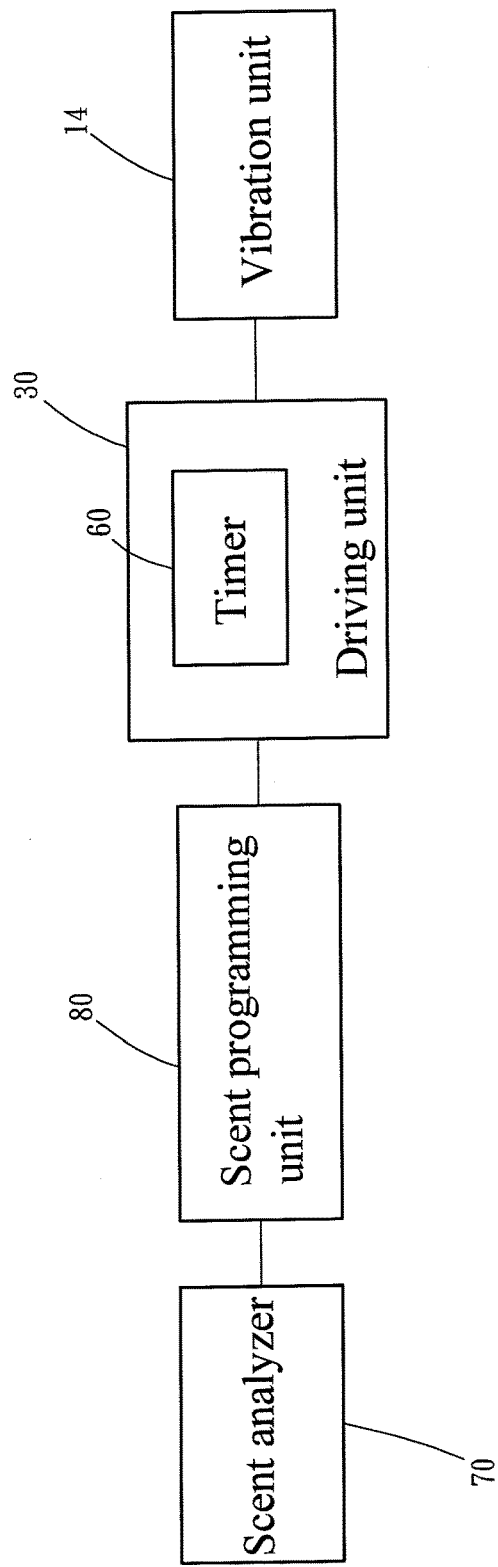
FIG. 5B is a schematic diagram of electrical connections of a driving unit according to the fifth embodiment of the disclosure.

FIG. 5A shows a schematic diagram of a structure according to a fifth embodiment of the disclosure. FIG. 5B shows a schematic diagram of electrical connections of a driving unit according to the fifth embodiment of the disclosure. Referring to FIGS. 5A and 5B, compared to the first embodiment, in this embodiment, the miniature scent generating device comprises a plurality of scented components 10. The scented components 10 are provided in an array arrangement so that the scented components 10 are densely located for facilitating a programmed scent blending management. Further, a plurality of granular materials having different scents are provided in the chamber 12 of each of the scented components 10. For example, in this embodiment, the chamber 12 of one scented component 10 is provided with a plurality of the granular first materials 20 having the first scent, whereas the chamber 12 of another scented component 10 is provided with a plurality of granular second materials 50. The first materials 20 and the second materials 50 respectively have different first and second scents.

Further, in the fifth embodiment, the driving unit 30 is electrically connected to the scent programming unit 80 having a built-in driving program of various scent data. According to the scent data, the scent programming unit 80 drives and activates the vibration units 14 in the scented components 10 to release different materials, so as to generate a blended scent conforming to a scent set by the scent data. Moreover, the scent programming unit 80 is further electrically connected to a scent analyzer 70. Accordingly, the scent analyzer 70 performs analysis of a target scent, generates scent information associated with the target scent, and transmits the scent information to the scent programming unit 80 to store the scent information in the scent programming unit 80. When the target scent is to be generated by the miniature scent generating device, the scent programming unit 80 programs the scent information transmitted from the scent analyzer 70, so as to prompt the driving unit 30 to drive and vibrate the vibration unit 14 to release the material needed for correspondingly generating the target scent. For example, the first materials 20 and the second materials 50 are released, and a blended scent is formed by blending the first scent and the second scent to reconstruct the target scent. It should be noted that, the above electrical connections refer to a communication status achieved through direct connections of currents, or wired or wireless signal connections of networks.

With the embodiments, it is illustrated that by the design of the first materials and the vibration unit of the disclosure, the first scent is released through generating the airflow of perturbation. Therefore, the disclosure has the advantage of being immune from issues of having a tendency of spoilage due to frequent heating, needing an additional different lighting source required for triggering the photocatalyst and suffering a complication in controlling the release amount of a scented substance. Further, different granular particles having different scents are respectively disposed in the scented components in the array arrangement. According to the built-in scent data, the scent programming unit drives the vibration unit to release the materials corresponding to the target scent, and thus to reconstruct a blended scent by blending the materials as the target scent. Accordingly, the miniature scent generating device may be jointly implemented with a mobile device, e.g., a smart phone, so that analysis and reconstruction of various scents can be readily performed at all times. For example, through transmission via the Internet or wireless communications, a scent can be analyzed at one location and reconstructed at another location. For another example, the miniature scent generating device may be implemented in popular three-dimensional glasses, so that an user is allowed to smell a scent associated with an environment displayed by a three-dimensional image while watching the three-dimensional image, thereby achieving diversified sensory satisfactions in visual and smell perspectives.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A miniature non-atomizer type scent generating device, comprising:
    two scented components, provided in an array arrangement, each scented component comprising a housing, a chamber located in the housing, a ventilation opening penetrating through the housing to communicate with the chamber, and a vibration unit disposed in the chamber;
    a plurality of first solid-state scented particles or first microcapsules encapsulating essences and a plurality of second solid-state scented particles or second microcapsules encapsulating essences disposed in two chambers correspondingly, wherein the first solid-state scented particles or first microcapsules encapsulating essences and the second solid-state scented particles or second microcapsules encapsulating essences respectively have a first scent and a second scent; and
    a driving unit comprising a control circuit, connected to two vibration units;
    wherein each of the two vibration units is controlled by the driving unit to produce a back and forth vibration which directly pushes gas inside the chamber and accordingly induces a unidirectional airflow of perturbation in the chamber;

wherein the unidirectional airflow of perturbation accompanies the first solid-state scented particles or first microcapsules encapsulating essences, or the second solid-state scented particles or second microcapsules encapsulating essences flowing through the ventilation opening and out of the chamber to enhance the blending and dispersing of a blended scent of the first scent and the second scent;

wherein each of the two vibration units comprises:

a piezoelectric film layer;

a first electrode layer, connected to the piezoelectric film; and a second electrode layer, connected to the piezoelectric film;

wherein the piezoelectric film layer is sandwiched between the first electrode layer and the second electrode layer, and the first electrode layer and the second electrode layer are respectively electrically connected to the driving unit to generate a varying electric field at the piezoelectric film to cause the piezoelectric film layer to produce the vibration.

2. The miniature non-atomizer type scent generating device of claim 1, wherein the housing comprises an upper housing and a lower housing corresponding to the upper housing, the ventilation opening penetrates through the upper housing, and the chamber is disposed between the upper housing and the lower housing.

3. The miniature non-atomizer type scent generating device of claim 1, wherein the driving unit comprises a timer for controlling a vibration period of the vibration unit.

4. The miniature non-atomizer type scent generating device of claim 1, wherein the driving unit is electrically connected to a scent programming unit.

5. The miniature non-atomizer type scent generating device of claim 4, wherein the scent programming unit is electrically connected to a scent analyzer.

6. The miniature non-atomizer type scent generating device of claim 2, wherein the lower housing is a semiconductor chip.

7. The miniature non-atomizer type scent generating device of claim 1, wherein the driving unit is located outside the housing.

8. The miniature non-atomizer type scent generating device of claim 1, wherein the scented components are fabricated by a micro electrical mechanical system (MEMS) process to achieve a miniaturized design.

9. A miniature non-atomizer type scent generating device, comprising:

a scented component including a housing, a chamber located in the housing, a ventilation opening penetrating the housing to communicate with the chamber, and a vibration unit disposed in the chamber;

a plurality of solid-state scented particles or microcapsules encapsulating essences disposed in the chamber and having a scent; and a driving unit comprising a control circuit and connected to the vibration unit;

wherein the vibration unit is controlled by the driving unit to produce a back and forth vibration which directly pushes gas inside the chamber and accordingly induces a unidirectional airflow of perturbation in the chamber;

wherein the unidirectional airflow of perturbation accompanies the solid-state scented particles or microcapsules encapsulating essences flowing through the ventilation opening and out of the chamber to enhance the dispersing of the scent;

wherein the vibration unit comprises:

a piezoelectric film layer;

a first electrode layer, connected to the piezoelectric film; and a second electrode layer, connected to the piezoelectric film;

wherein the piezoelectric film layer is sandwiched between the first electrode layer and the second electrode layer, and the first electrode layer and the second electrode layer are respectively electrically connected to the driving unit to generate a varying electric field at the piezoelectric film to cause the piezoelectric film layer to produce the vibration.

10. The miniature scent generating device of claim 9, wherein the driving unit comprises a timer for controlling a vibration period of the vibration unit.

11. The miniature scent generating device of claim 9, wherein the housing comprises an upper housing and a lower housing corresponding to the upper housing, the ventilation opening penetrates through the upper housing, and the chamber is disposed between the upper housing and the lower housing.

12. The miniature non-atomizer type scent generating device of claim 11, wherein the lower housing is a semiconductor chip.

13. The miniature non-atomizer type scent generating device of claim 9, wherein the driving unit is located outside the housing.

14. The miniature non-atomizer type scent generating device of claim 9, wherein the scented component is fabricated by a micro electrical mechanical system (MEMS) process to achieve a miniaturized design.

* * * * *